(12) United States Patent
Polo (10) Patent No.: US 9,055,967 B1
(45) Date of Patent: Jun. 16, 2015

(54) TISSUE SEVERING DEVICE HAVING DUAL RECIPROCATING LOOPED BLADES AND METHODS OF USE

(71) Applicant: Oscar R Polo, Portland, OR (US)

(72) Inventor: Oscar R Polo, Portland, OR (US)

( * ) Notice: Subject to any disclaimer, the term of this patent is extended or adjusted under 35 U.S.C. 154(b) by 0 days.

(21) Appl. No.: 14/536,500

(22) Filed: Nov. 7, 2014

(51) Int. Cl.
*A61B 17/32* (2006.01)

(52) U.S. Cl.
CPC . *A61B 17/32002* (2013.01); *A61B 2017/32006* (2013.01); *A61B 2017/320024* (2013.01); *A61B 2017/320028* (2013.01)

(58) Field of Classification Search
CPC ............... A61B 17/32002; A61B 17/320758; A61B 17/1608–17/1611; A61B 2017/320024; A61B 2017/32006; A61B 2017/320028; A61B 2017/320032; A61B 2017/32004; A61B 2017/320775; B26B 7/00; B26B 7/005
USPC ............... 606/171, 167, 170, 177, 180, 83; 30/304
See application file for complete search history.

(56) References Cited

U.S. PATENT DOCUMENTS

| | | | | |
|---|---|---|---|---|
| 5,222,959 A * | 6/1993 | Anis | 606/107 |
| 5,443,472 A * | 8/1995 | Li | 606/114 |
| 5,810,806 A * | 9/1998 | Ritchart et al. | 606/45 |
| 5,851,212 A * | 12/1998 | Zirps et al. | 606/167 |
| 5,925,056 A * | 7/1999 | Thomas et al. | 606/180 |
| 5,983,499 A * | 11/1999 | Andrews | 30/29.5 |
| 6,156,043 A * | 12/2000 | Krahn | 606/110 |
| 2005/0080441 A1* | 4/2005 | Dodge et al. | 606/171 |
| 2005/0177168 A1* | 8/2005 | Brunnett et al. | 606/80 |
| 2008/0103412 A1* | 5/2008 | Chin | 600/566 |
| 2008/0249552 A1* | 10/2008 | Eliachar et al. | 606/171 |
| 2008/0249553 A1* | 10/2008 | Gruber et al. | 606/171 |
| 2009/0125036 A1* | 5/2009 | Bleich | 606/110 |
| 2009/0182361 A1* | 7/2009 | Thompson et al. | 606/159 |
| 2011/0257651 A1* | 10/2011 | Jenkins | 606/48 |
| 2011/0307001 A1* | 12/2011 | Becker | 606/192 |
| 2013/0018402 A1* | 1/2013 | Polo | 606/170 |
| 2013/0172828 A1* | 7/2013 | Kappel et al. | 604/272 |
| 2013/0274751 A1* | 10/2013 | Steinwachs et al. | 606/84 |
| 2013/0296847 A1* | 11/2013 | Germain et al. | 606/39 |
| 2014/0018834 A1* | 1/2014 | Kather et al. | 606/172 |

* cited by examiner

*Primary Examiner* — Julian W Woo
*Assistant Examiner* — Shaun L David
(74) *Attorney, Agent, or Firm* — Baumgartner Patent Law; Marc Baumgartner (57) ABSTRACT

Tissue severing devices having dual reciprocating looped blades are disclosed herein. The severing devices described herein can be used during laparoscopic surgery to cut tissue of a predetermined diameter using the two looped blades.

21 Claims, 11 Drawing Sheets

TISSUE SEVERING DEVICE HAVING DUAL RECIPROCATING LOOPED BLADES AND METHODS OF USE

FIELD OF THE INVENTION

The teachings herein relate to instruments useful in laparoscopic surgery and methods of using said instruments. More specifically, the embodiments herein relate to tissue severing devices having dual reciprocating looped blades and methods of using these devices to cut tissue from a patient.

BACKGROUND

During laparoscopic surgical procedures and, more particularly, tissue removal procedures, it is desirable to limit the size of the entry incision to minimize the trauma experienced by the patient. In the past, efforts to minimize entry incision size have generally been limited due to the size of the tissue to be removed and the need for access to the tissue.

Morcellators are devices that morcellate, or cut tissue, into smaller pieces to allow for easier removal through small surgical access sites. Prior art morcellators that require a pushing or downward traction operation to cut the tissue present a danger of over extension into tissue that is not to be injured. By way of example, but not limited thereto, during a laparoscopic subtotal hysterectomy, one way of minimizing the danger of this over extension is to amputate the body of the uterus from the cervix prior to morcellation. The amputation of the uterus presents an added risk of injury to other nearby organs, such as the rectum and bowel, as they lie behind the uterus and are difficult to see during uterus amputation. Also, amputation is commonly performed using electrocautery or harmonic scalpel which may cause lateral spread of heat or other energy and can inadvertently cause a burn to the bowel or bladder that may not be realized until days after surgery. Further, amputation of the uterus requires the use of one surgical instrument to amputate the uterus and another surgical instrument to morcellate the uterus with their associated cost and complexity of use.

Some known laparoscopic morcellators utilize graspers that pull tissue into a spinning tubular blade or the spinning blade is pushed into the tissue. These types of instruments have their limitations and dangers associated with their use, non-exclusively including the exposed sharp blade possibly injuring surrounding tissue not intended to be morcellated, discharge of the tissue in a spinning tool, and the difficulty and dangers of placing downward traction into the target tissue. Currently, performing a morcellation through a laparoscope is difficult as there are concerns about a spinning blade being pointing downward toward the bowel. It is undesirable to use a spinning blade that spits cut tissue throughout the abdominal cavity and that allows for cut tissue to drop onto other organs (bowel) in the abdominal cavity. Furthermore, these morcellators require both hands to be used by a surgeon, one to hold the spinning morcellator and the second for the grasper that pulls the tissue through it. The need for two hands to morcellate the tissue limits the surgeon to use his other hand to hold another instrument or the laparoscope. Also, the need for a two handed approach disallows the ability to design the instrument to be used robotically.

In order to make laparoscopic tissue removal safer without the need to first amputate the tissue, morcellators were designed to have a single, looped blade. According to one prior art embodiment, a blade was designed to oscillate, such that the ends of the single looped blade were configured to be rapidly and alternatively pulled on in a proximal direction to impart a sawing motion to the cutting element's distal end. See, for example, U.S. Pat. No. 8,585,727 "Tissue Severing Devices and Methods". However, while improving upon the safety of prior art morcellators, the efficacy of using a single looped blade knife is markedly diminished by the short distance that the blade travels back and forth to make the cut. Another disadvantage with an oscillating single looped blade is that the targeted tissue moves in the same direction as the blade, making the attempted cut more difficult to perform.

Accordingly there is a need in the art to provide morcellator blade assemblies that are safe for the patient, such that they cut in a proximal direction away from the targeted tissue and nearby organs and oscillate so that they don't splinter and hurl tissue into the surrounding area as with a spinning blade. Additionally the assemblies should also be more efficient at cutting the targeted tissue than a single looped blade. The following disclosure describes cutting devices that solve this need in the art by utilizing reciprocating dual looped blades.

Preferred embodiments are directed to tissue cutting devices comprising: an electric motor configured to be turned on and off; an external tube having an internal channel traversing lengthwise from proximal to distal ends; first and second extension members having proximal and distal ends, left and right sides, and positioned superiorly and inferiorly to one another within the internal channel of the external tube such that they traverse parallel with the length of the external tube, wherein the proximal ends of the extension members are operably coupled to the electric motor that drives straight reciprocating motion of the first and second extension members in alternate proximal and distal directions with respect to each other, such that when the first extension member is pushed distally the second extension member is pulled proximally, and vice versa; an outer looped blade having a first end operably coupled to the first extension member; and a second end operably coupled to the second extension member; and an inner looped blade, positioned proximally and adjacent to the outer looped blade, and having a first end operably coupled to the first extension member and a second end operably coupled to the second extension member; and wherein the outer and inner looped blades are positioned distally to the distal end of the external tube, and configured to reciprocate in alternate clockwise and counter-clockwise directions and in opposite directions with respect to each other as the first and second extension members reciprocate proximally and distally.

Additional embodiments are directed to methods of cutting tissue from a patient comprising: providing the tissue cutting device; inserting the distal end of the external tube into the patient; pulling the external tube proximally exposing the looped blades; turning the electrical motor on to reciprocate the outer and inner looped blades in alternating clockwise and counter-clockwise directions; cutting the tissue from the patient with the reciprocating outer and inner looped blades; pushing the external tube distally over the looped blades; and removing the external tube from the patient.

BRIEF DESCRIPTION OF THE DRAWINGS

It will be appreciated that the drawings are not necessarily to scale, with emphasis instead being placed on illustrating the various aspects and features of embodiments of the invention, in which.

DETAILED DESCRIPTION OF THE ILLUSTRATED EMBODIMENTS

Embodiments of the present invention are described below. It is, however, expressly noted that the present invention is not limited to these embodiments, but rather the intention is that modifications that are apparent to the person skilled in the art and equivalents thereof are also included.

Embodiments herein relate to a reciprocating severing device can be used in laparoscopic surgery to cut tissue in cylindrical shaped (or other desired shapes such as oval, arched, and the like) pieces of a predetermined diameter. Once cut up, the pieces can be pulled through a trocar sleeve of a larger inside diameter.

Figure 1:
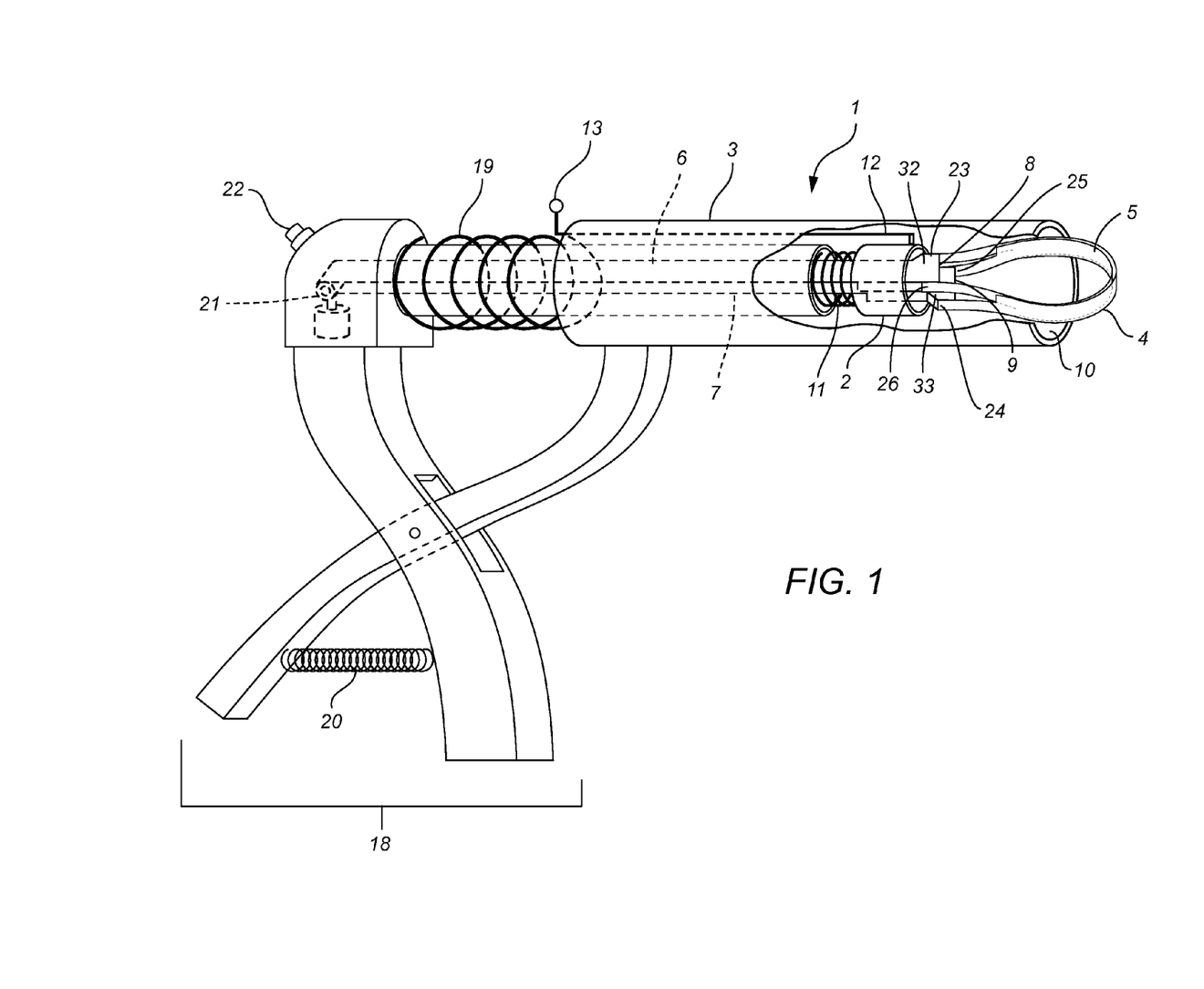
FIG. 1 is a perspective view of a cutting device in its neutral or closed position.
Figure 2:
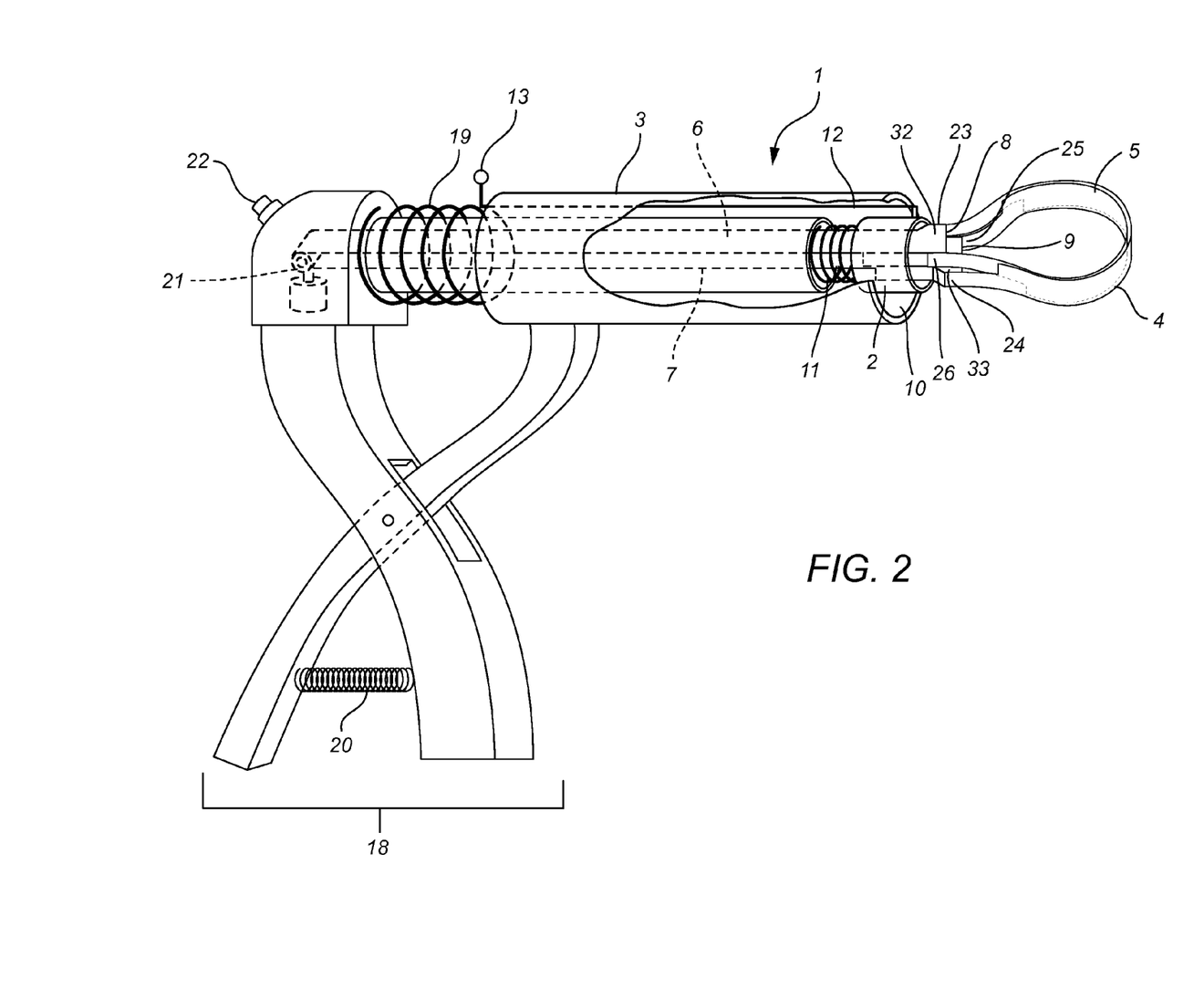
FIG. 2 is a perspective view of a cutting device in a partially extended position.
Figure 3:
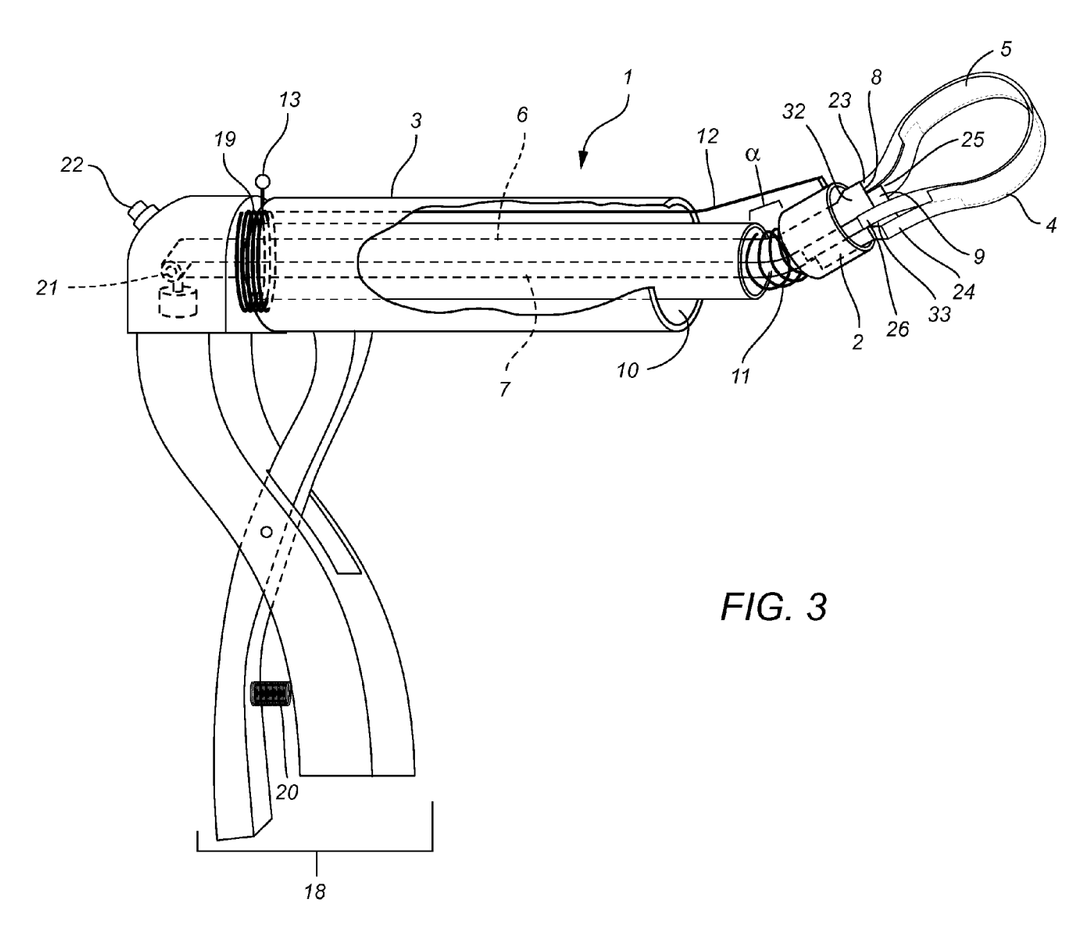
FIG. 3 is a perspective view of a cutting device in its fully extended position.

FIGS. 1-3 show perspective views of a preferred cutting device 1. The device 1 preferably includes two extension members, such as the rods 6 and 7, positioned within an internal tube 2 that is positioned within an external tube 3. The extension members, e.g., rods 6 and 7, internal tube 2 and external tube 3 each have proximal and distal ends and preferably run along the same axis. More specifically, it is preferred that the extension members, e.g., rods 6 and 7 include a superior extension member 6 and an inferior extension member 7 and that they are fixed parallel to one another, but configured to move in proximal and distal directions.

Figure 12:
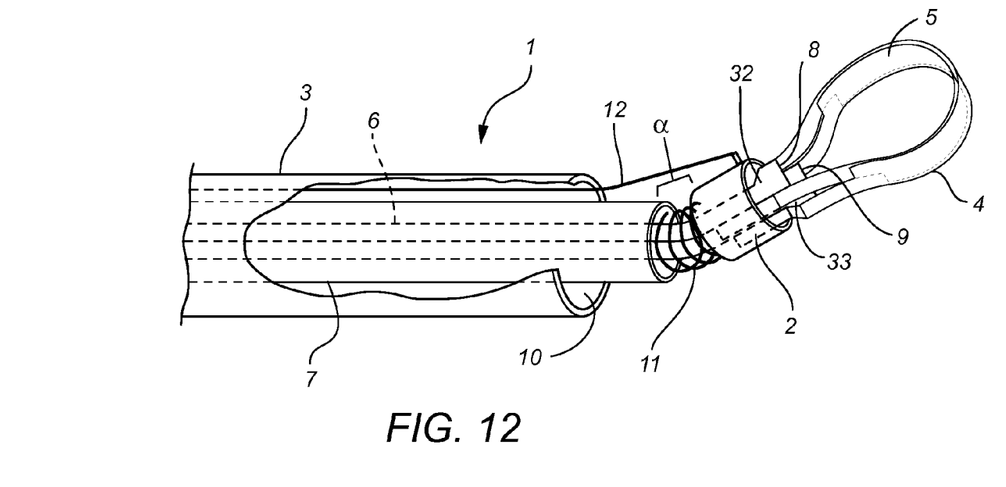
FIG. 12 is a close up view of a cutting device in a fully extended position.

Preferably, the extension members, e.g., rods 6 and 7 are flexible to allow bending as shown in FIGS. 3 and 12. However, it is preferable that the distals ends of the extension members 6 and 7 (distal to the bendable neck 7) are sufficiently rigid so the blades 4 and 5 do not bend while cutting. Alternatively, the extension members can be substantially rigid throughout and have necks that are bendable and that are aligned with a bendable neck 11 of the internal tube 2. In yet another embodiment, not shown, both the inner tube and rods are flexible and symmetrically bend during flexion. In all embodiments, the outer tube remains rigid. Suitable materials for the extension members include thin flexible yet strong metals, including nitinol and stainless steel (e.g., spring steel), or fiberglass, for example. Additionally, embodiments can be directed to extension members, that are substantially rigid and don't bend.

Figure 14:
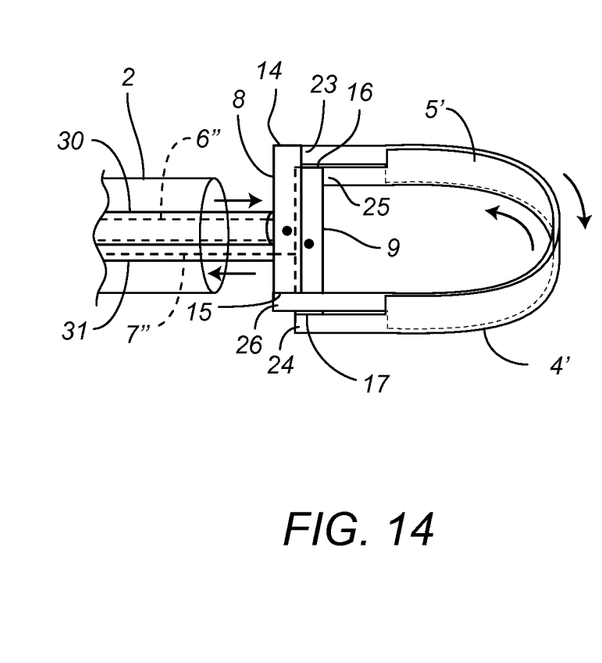
FIG. 14 is a close up view of cables within barrels coupled to U-shaped blades and crossbars, showing motion.

The reciprocating extension members can have any suitable cross-section, including circular, semicircular, oval, square, hexagon, polygonal, rectangular, and the like. Likewise while the term rods are used predominantly herein, the broader term "extension member" is meant to encompass both rods 6 and 7 or ribbons 6' and 7' or cables 6" and 7", and these terms can readily be substituted where suitable. As shown in FIG. 14, to keep cables 6" and 7" in an inferior to superior relationship, the inside tube can include an inferior rigid barrel 31 and a superior rigid barrel 30, that sheath their respective cables 6" and 7".

Figure 13:
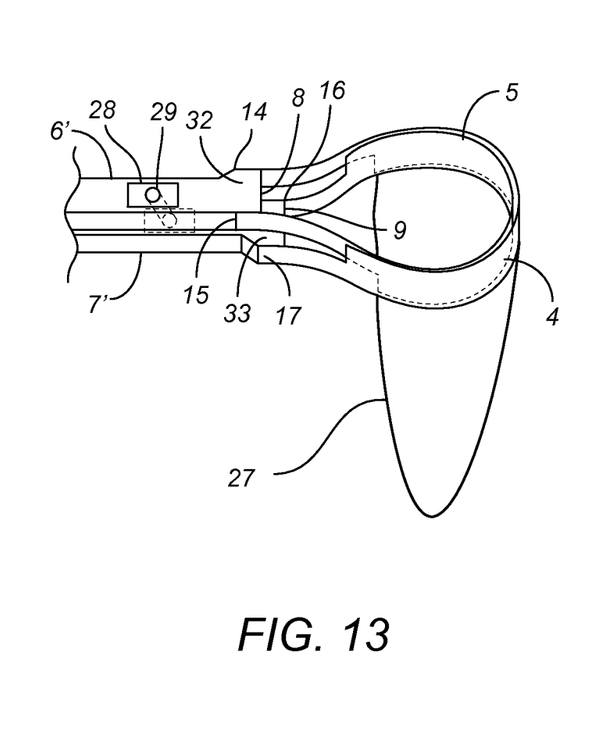
FIG. 13 is a close up view of ribbons coupled to oval shaped blades with a catching bag.

As shown in FIG. 13, for ribbon embodiments, it is preferred that the parallel ribbons 6' and 7' are positioned with their flat sides facing towards inferior and superior directions, with the superior ribbon 6' positioned above the inferior ribbon 7'. During motion, to keep the ribbons from bowing away from each other, a segmental slot 28 can be located on one ribbon 6' and a pin 29 is fixed to the second ribbon 7' and configured to stay within the slot 28 such that the ribbons 6' and 7' will not detach nor bow away from each other. The positioning of the segmental slot 28 and pin 29 shown in FIG. 13 can be interchanged between the ribbons 6' and 7'. The slot length 28 is at least of the length of the maximum difference of proximal/distal travel of the reciprocating ribbons 6' and 7' (stroke length). Preferably ribbons 6' and 7' are made of a flexible material with sufficient strength (rigidity) to maintain its shape when pushing and pulling the blades 4 and 5. This can be a flexible thin material such as spring steel or nickel titanium, also known as nitinol, or fiberglass, for example.

The extension members, e.g., rods 6 and 7 are coupled to an electric motor 21 that has mechanical means for rapidly reciprocating the rods 6 and 7 such that they travel in straight trajectories, each alternating from a proximal to distal direction. More specifically, when the superior rod 6 is being pushed in a distal direction, the inferior rod 7 is simultaneously being pulled in a proximal direction, and vice versa. Preferably the motor 21 is positioned at the proximal end of the device 1 and is operably coupled to the proximal ends, or substantially so, of the extension members, e.g., rods 6 and 7. An alternative is to have the motor, a stand alone unit, separate from the instrument and attached to the reciprocating gear system via a cable. A power control, such as a switch 22, operably coupled to a power source (e.g., batteries, electrical plug) can be used to turn the motor 21 on and off. A dial, not shown, can also be used to adjust the motor 21 to control the reciprocation speed of the extension members, e.g., rods 6 and 7.

Depending on the blade shape, a crossbar 8 may or may not be used with the embodiments described herein. For oval shaped blades 4 and 5, shown in FIG. 5A, it is preferred that the crossbars 8 and 9 are not used, and that the outer blades couple directly to the ends of the extension members 6 and 7. For these embodiments, while parallel, the extension members 6 and 7 are preferably staggered or offset from each other slightly in opposite directions at their distal ends, in the left/right plane, by 1 mm or less. The offset can be in the form of flares 32 and 33 (FIG. 5A) or cutouts 34 and 35 (FIG. 5B). The offset only needs to be slight, such as the thickness of the blades 4 and 5, and is incorporated so that the blades 4 and 5 don't interfere with each other as they reciprocate. For example, and as shown in FIGS. 1, 2, 3, and 5A the distal end 32 of the superior rod 6 is flared to the left, while the distal end 33 of the inferior rod 7 is flared to the right. Similarly as shown in FIG. 5B, the left distal end of the superior rod is cutout 34 and the right distal end of the inferior rod is cutout 33. The flares 32 and 33 or cutouts 34 and 35 are preferably offset the same lateral distance (e.g., 1 mm or less). The flares 32 and 33 should not be flared too wide in the left/right lateral plane that they cannot fit within the distal opening 10 of the external tube 3, when the blades 4 and 5 are retracted within. As in the rods, it is preferred that the distal ends of the ribbons 6' and 7' are offset from each other with flares 32 and 33 in the right/left plane.

Figure 5A:
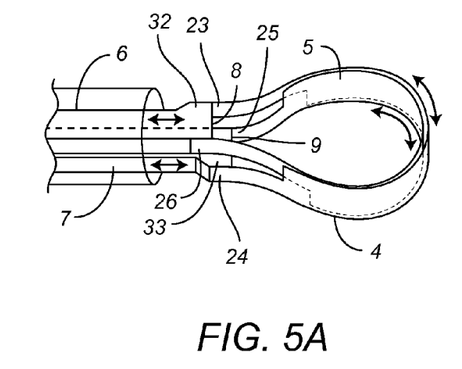
FIG. 5A is a close-up perspective view of oval shaped looped cutting blades, with extension members having flared distal ends, and showing motion.
Figure 5B:
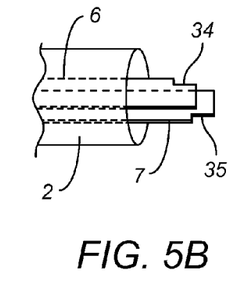
FIG. 5B is a close-up perspective view of extension members having cutouts at their distal ends for use with oval shaped looped cutting blades (not shown).

FIG. 5A shows how the oval blades 4 and 5 couple to the distal ends of their extension members 6 and 7. The outer blade 4 comprises a left end 23 coupled to the flared left end 32 of the superior extension member 6 and a right end 24 coupled to the right flared end 33 of the inferior extension member 7. Similarly, the inner blade 5 comprises a left end 25 coupled to the non-flared left end of the inferior extension member 7 and a right end 26 coupled to the non-flared right end of the superior extension member 6. With respect to FIG. 5B, the outer blade's 4 left end 23 couples to the non-cutout left end of the superior extension member 6 and the right end 24 couples to the non-cutout right end of the inferior extension member 7. Similarly, the inner blade's 5 left end 25 couples to the cutout left end 34 of the inferior extension member 7 and the right end 26 couples to the cutout right end 35 of the superior extension member 6.

Figure 4A:
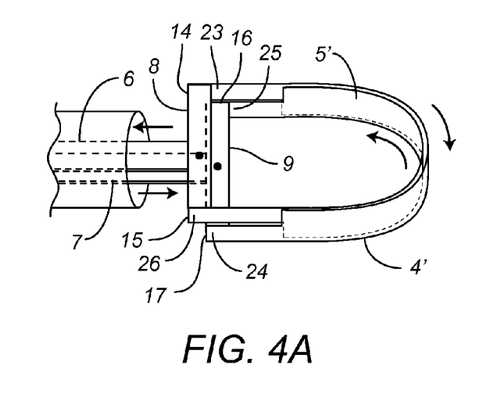
FIG. 4A is a close-up top perspective view of U-shaped looped cutting blades, with a crossbar, showing reciprocating motion in a first direction.
Figure 4B:
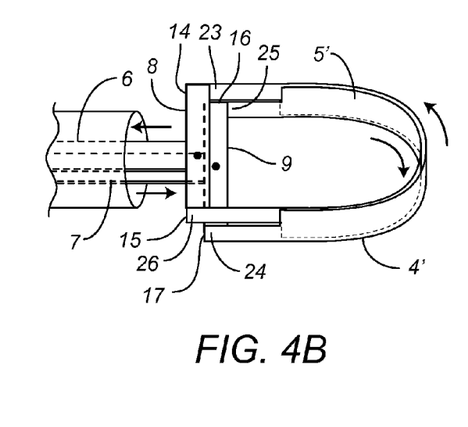
FIG. 4B is a close-up top perspective view of U-shaped looped cutting blades, with a crossbar, showing reciprocating motion in a second direction.

In contrast, for U-shaped blades 4' and 5', shown in FIGS. 4A and 4B, it is preferred that a superior and inferior crossbars 8 and 9 are attached to the distal ends of their respective extension member 6 and 7. When crossbars are used, a superior crossbar 8 is positioned perpendicular to and at the distal end of the superior extension member 6. Preferably, the superior extension member 6 couples to the superior crossbar 8 near the middle, offset by less than 1 mm in one direction, of the crossbar 8. Similarly, an inferior crossbar 9 is positioned perpendicular to and at the distal end of the inferior extension member 7. Preferably, the inferior extension member 7 couples to the inferior crossbar 9 near the middle, offset in the opposite direction by less than 1 mm, of the crossbar 9. It is preferred that the coupling between the crossbars 8 and 9 with their respective rods 6 and 7 is a fixed coupling that doesn't allow the crossbars 8 and 9 to rotate around the rods 6 and 7 during operation. The crossbars 8 and 9 are configured to alternate traveling in the proximal/distal directions with their respective extension members 6 and 7.

It is advantageous to have the crossbars 8 and 9 be the same length or substantially so. The superior and inferior crossbars 8 and 9 are parallel to each other, and individually have left (14 and 16) and right (15 and 17) ends. It is preferred that the crossbars 8 and 9 are offset left to right the same distance, and as shown in the cross-section view of FIGS. 6 and 7. While the superior crossbar 8 is shown extending farther left than the inferior crossbar 9, these offsets can readily be interchanged such that the inferior crossbar 9 extends farther right than the superior crossbar 8. For these embodiments, while parallel and the same length, the cross bars 8 and 9 are preferably staggered or offset from each other slightly in opposite directions in the left/right plane by 1 mm or less. The offset only needs to be slight, such as the thickness of the blades 4' and 5', and is incorporated so that the blades 4' and 5' don't interfere with each other as they reciprocate.

Figure 6:
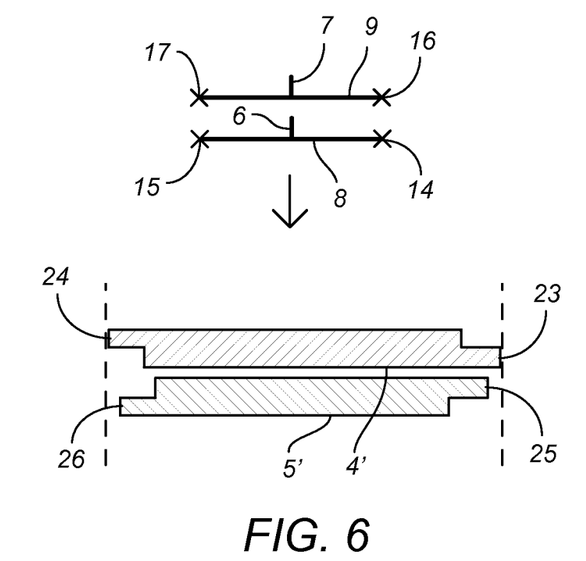
FIG. 6 shows cross sections of crossbars and the blades in a straightened configuration.
Figure 7:
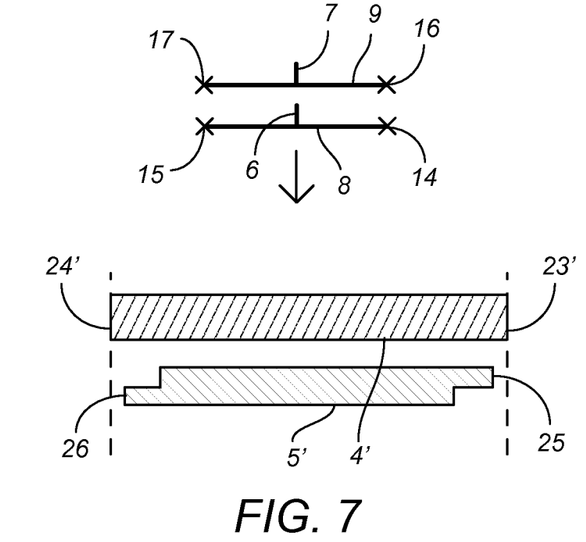
FIG. 7 shows cross sections of crossbars and the blades in a straightened configuration.
Figure 8:
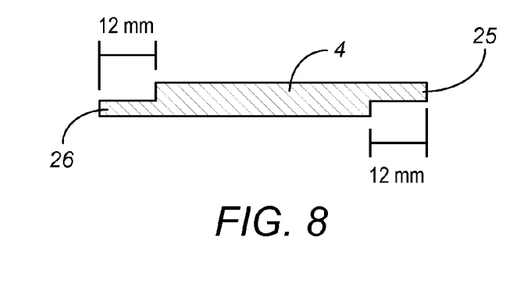
FIG. 8 shows a straightened view of an inner blade with extensions.

With reference to FIGS. 4A and 4B, the outer U-shaped blade 4' comprises a left end 23 coupled to the left end 14 of the superior crossbar 8 and a right end 24 coupled to the right end 17 of the inferior crossbar 9. Similarly, the inner U-shaped blade 5' comprises a left end 25 coupled to the left end 16 of the inferior crossbar 9 and a right end 26 coupled to the right end 15 of the superior crossbar 8. FIGS. 6 and 7 illustrate straightened and detached views of the outer blade 4' and the inner blade 5' in context with their coupling points 14-17 on the crossbars 8 and 9. As shown in this view, the outer blade 4 is preferably longer than the inner blade 5 (e.g., 1-3 mm longer, for example), as it traverses a longer distance in connecting the outer ends 17 and 14 of the crossbars 8 and 9, in contrast to the inner blade 5 which traverses a shorter distance in connecting the inner ends 15 and 16 of the crossbars 8 and 9. Thus when in the loop configuration, such as shown in FIGS. 4A, 4B and 5A, 5B, the outer blade 4 has a slightly larger diameter than the inner blade 5. The blades 4 and 5 preferably touch, but glide past each other when cutting.

All blades described herein 4' and 5' preferably have side extensions 23-26, that are shown in FIGS. 6-10 for example. While the outer blade 4' does not need extensions 23 and 24, the inner blade 5' should have extensions 25 and 26 for the invention to function as described herein. FIG. 7, shows an embodiment where the inner blade 5' has extensions 25 and 26 but the outer blade 4' lacks extensions and just has a left end 23' and right end 24'. Extensions are used herein because while the blades cross over from one extension member (crossbar) to another, they remain in the same plane and parallel to each other. Without the extensions 25 and 26 the inner blade 5' would collide with the flared distal ends 32 and 33 of the extension members 6 and 7, or the ends of the crossbars 8 and 9 that attach to the outer blade 4. Either the blade ends 23' 24' or extensions 23-26 of the blades can couple to the extension members 6 and 7 or crossbars 8 and 9 in similar ways. The height of the blade ends 23' 24' or extensions 23-26 is preferably the same width as the thickness of the distal ends of the extension members, e.g., rods, crossbars. If the inner blade 5 has blade ends 23' 24' or extensions 23-26 wider than the thickness of the distal ends of an extension member 6 or 7 then it could potentially collide with the other extension member 6 or 7 during operation. For example, if the extension member's distal ends (where they couple to the blade ends 23' 24' or extensions 23-26) are 4 mm wide then they each can be 2 mm thick and still slide through the 8 mm external tube. Therefore the width of the blade ends 23' 24' or extensions 23-26 can be 2 mm in width. The length of the extensions 23-26 is preferably equivalent to the distance traveled by the blade. Thus if the blade 5' was traveling back and forth 12 mm, during the reciprocating cutting, the left extension 25 would be 12 mm and the right extension 26 would be 12 mm. Likewise for the outer blade 4'. Preferred travel of the blades is greater than 10 mm.

Figure 9:
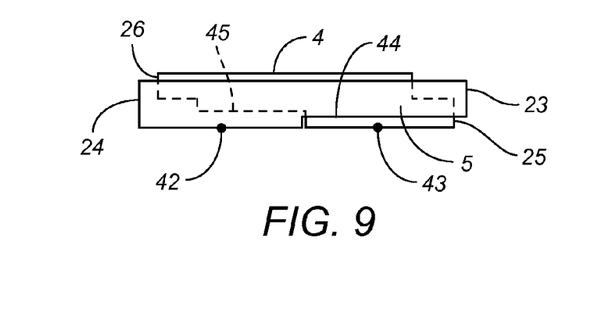
FIG. 9 shows straightened inner and outer blades with backstops aligned with each other.
Figure 10:
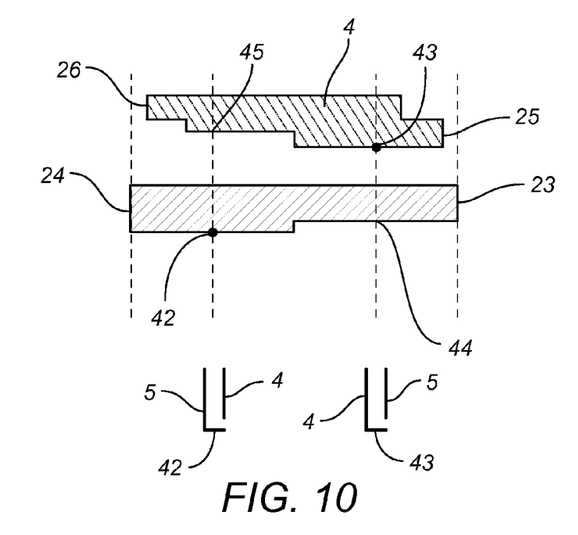
FIG. 10 shows straightened inner and outer blades with backstops separated from each other.

When cutting there is counter traction by the tissue on the blades 4 and 5. Left alone, this counter traction could potentially result in one blade being pushed inferior to the other blade during cutting. This would undesirably result in a separation of the sharp edges (e.g., superior edges) from the same plane, such that the inferiorly pushed blade no longer contacts the targeted tissue, thereby making it ineffective. FIGS. 9 and 10 provide straightened views of blades 4 and 5 with back stops 42 and 43 that are designed to prevent the above concern. These backstops 42 and 43 are small extensions, one backstop 42 is positioned mid-lateral, on the inferior end of the inner blade 5 and the other backstop 43 is positioned on the opposite side, mid-lateral, on the inferior end of the outer blade 4. The blade opposite the backstops 42 and 43 has been cut slightly shorter at its inferior end, so that it can glide over the backstop. This cut out segment is at least the length of the distance traveled by the extension members 6 and 7. During operation, the cut out segment 45 of the inner blade 4 slides over the backstop 42 of the outer blade 5. Similarly the cut out segment 44 of outer blade 5 slides over the backstop 43 of the inner blade 4.

As the blades 4 and 5 described herein individually complete a loop, it is preferred that they are made of a sufficiently flexible material that also has sufficient strength for cutting through targeted tissue. This can include flexible thin metals (less than 1 mm thick, such as between 0.5-1 mm.) such as nickel titanium, also known as nitinol. Additionally the blades 4 and 5 can be made of a metal alloy, or suitable composite materials such as carbon fiber, for example. The devices 1 herein are designed to use the edge of the blades 4 and 5 for cutting, so it is preferred that the blades have at least one edge configured to cut into tissue, but preferably it is the superior edges of the blades. The cutting edge or edges of the blades 4 and 5 can be smooth or serrated. According to other embodiments designed to prevent the blades from moving off plane a slider mechanism similar to that used in FIGS. 13 and 19 can be used. According to this embodiment, either the outer or inner looped blade has a pin, and the other looped blade has a slot configured to keep the blades together and allow the pin to reciprocate within the slot, as the blades move in clockwise and counter-clockwise directions. Preferably the pin and slot are positioned at the most distal end of the looped blades. The slot length is at least equal to or longer than the stroke length of the extension members.

Preferred blades 4 and 5 described herein, are configured to cut cylindrical shaped tissue, or substantially so of a predetermined thickness, to fit through a trocar sleeve of a predetermined diameter. The blades 4 and 5 can be looped to shapes including: circular, omega-shaped (Ω), oval, square, U-shaped, or substantially similar variants. Preferred blades have curved sides and lack straight sides, and angles of 120 degrees or less, accordingly V-shaped or polygon shaped blades (e.g., squares, rectangles, hexagons rhombuses) are not preferred. It is preferred that both blades 4 and 5 are configured into the same shape, with the inner blade 5 being slightly shorter than the outer blade 4. FIGS. 4A and 4B illustrate a U-shape configuration of blades 4' and 5' while oval shaped blades 4 and 5 are shown in FIG. 5A. These shapes both are collapsible, are interchangeable with one another and with other suitable shapes for all embodiments herein, where applicable. The U-shape blades 4' and 5' are advantageous for embodiments wherein the crossbars 8 and 9 are used, while the oval shaped blades 4 and 5 are suited for embodiments wherein the crossbars 8 and 9 are not used, and the blades 4 and 5 are configured to collapse within the external tube 3 when they make contact with distal rim surrounding the opening 10.

Preferably the ends of the blades 4 and 5 are configured to releasably attachable to the crossbars 8 and 9 to make replacement of dull blades possible during operation, without having to replace the entire instrument. Any suitable releasable attachment means can be used for the blades 4 and 5 and the crossbars 8 and 9, including snaps, pins, slots, notches, tabs, locks, and the like. According to other embodiments, the blades 4 and 5 can be non-releasably attached to the crossbars 8 and 9 which are releasably attached to the rods 6 and 7, to allow for changing out new blades 4 and 5. Still further preferred embodiments relate to blades being non-releasably attached to crossbars, wherein the crossbars are non-releasably attached to the distal end of the rods, and the proximal ends of the rods are releasably attachable to the device, so that a user would change out old blades with a new rod/crossbar/blade assembly being inserted into the internal tube 2 and/or the external tube 3.

As mentioned above, the rods 6 and 7 are configured with the motor 21 to reciprocate rapidly back in forth in proximal and distal directions. This motion causes the blades 4' and 5' to oscillate such that one end (left/right) of a blade is being pulled proximally while the opposite end (left/right) of the same blade is being pushed distally. FIGS. 4A and 4B show how the reciprocating rods 6 and 7 cause the blades 4' and 5' to saw back and forth. In FIG. 4A, the superior rod 6 is pushing the superior crossbar 8 distally. This motion pushes the outer blade 4' in a clockwise direction, and pushes the inner blade 5' in a counter-clockwise direction. Simultaneously in FIG. 4A, the inferior rod 7 is pulling the inferior crossbar 9 proximally. This motion pulls the outer blade 4' in a clockwise direction, and pulls the inner blade 5' in a counter-clockwise direction. In FIG. 4B, the directional motions shown in 4A are reversed, such that the superior rod 6 is pulling the superior crossbar 8 proximally. This motion pulls the outer blade 4' in a counter-clockwise direction, and pulls the inner blade 5' in a clockwise direction. Simultaneously in FIG. 4B, the inferior rod 7 is pushing the inferior crossbar 9 distally. This motion pushes the outer blade 4' in a counter-clockwise direction, and pushes the inner blade 5' in a clockwise direction. Accordingly, the outer blade 4' and the inner blade 5' alternate between being pushed and pulled, where the outer blade 4' cuts in one rotational direction, while the inner blade 5' simultaneously cuts in an opposite rotational direction. This motion is similar for embodiments where crossbars are not used.

Preferred devices 1 described herein are configured such that the external tube 3 traverses along the same axis as the internal tube 2 that is fixed to the handle and positioned within the external tube 3. According to preferred embodiments, the looped blades 4 and 5 have a larger diameter than the distal opening 10 and are configured to collapse when the external tube 3 is pushed into its most distal position, as shown in FIG. 1. For embodiments shown in FIGS. 4A and 4B, the crossbars 8 and 9 have a longer length, from their left and right ends 14 to 15, and 16 to 17, than the diameter of the external tube 3 and are configured such that they can be collapsed/retracted into and opened/extended outward from a distal opening 10 of the external tube 3. Two preferred embodiments of retracting the crossbars 8 and 9 are shown in FIGS. 15-16 and FIGS. 17-18.

The collapsing of the blades 4 and 5 is shown in FIGS. 1-3. While crossbars are not shown in these figures, collapsible crossbars can be used with the same mechanisms described. Preferably, a tube spring 19 is positioned proximal to and operably coupled with the coaxial external tube 3. FIG. 1 illustrates the device 1 in its' neutral or closed position, where the tube spring 19 is in a fully uncompressed state. In this natural position, the external tube 3 is pushed forward to its maximum distal distance and thereby encloses the blades 4 and 5, either entirely or partially. In this state, the blades 4 and 5 are preferably compressed within the external tube 3, in comparison to their expanded state outside of the external tube 3.

A handle 18 (with or without a handle spring 20) can be operably coupled to the external tube 3 such that squeezing the handle 18 slides the external tube 3 in a proximal direction, thereby compressing the tube spring 19. Other suitable handle and/or trigger configurations can be used to manipulate the external tube 3 in distal and proximal directions as well. FIG. 2 illustrates the device 2 in a partially compressed state, with the handle 18 being partially squeezed, thereby moving the external tube 3 in a proximal direction, and thereby partially compressing the tube spring 19. The proximal sliding of the external tube 3 allows the distal end of the internal tube 2 and the blades 4 and 5 to be exposed from the external tube's opening 10. For crossbars (not shown) they would be extended distally outward from the external tube's opening 10 as well. Once released from the external tube 3, the flexible blades 4 and 5 can spring into their uncompressed looped or operational configurations, such as shown in FIGS. 2, 4A, 4B, and 5A, for example.

Preferred devices 1 described herein have a bendable neck 11 positioned on the internal tube 2 near the distal end, but proximal to the crossbars 8 and 9 and blades 4 and 5. The bendable neck 11 allows for the internal tube 2 to articulate in the superior direction, as shown in FIG. 3. Preferred a angles of full articulation include 30-45°, for example. The blades 4 and 5 are preferably perpendicular to the tissue being cut. The blades 4 and 5 may first need to be in a straight configuration (e.g., FIG. 2) to cut into the targeted tissue. As it cuts deeper into the tissue the sharp end (e.g., superior edge of the blades 4 and 5) is rotated proximally by bending the distal end as shown in FIG. 3. However as a user pulls the device 1 proximal the blades 4 and 5 continuously straighten out. This can be accomplished by straightening out the bendable neck 11 or by pivoting at the point of insertion of the trocar sleeve into the body. The bendable neck 11 is also advantageous in preventing the device 1 from getting jammed in the tissue or the handle 18 from hitting the side of the table or abdominal wall. Also it is more ergonomic for the user to be able to bend the neck 11 by squeezing the handle 18, keeping the wrist and arm in a more neutral position.

The bendable neck 11 can be similar to articulating necks described in U.S. Pat. No. 8,585,727 "Tissue Severing Devices and Methods" in particular: FIGS. 25 and 26 and descriptions thereof. This reference is expressly incorporated by reference herein in its entirety. Suitable mechanisms to allow for superior articulation may include, but not limited to, one or more pivots, joints (e.g., bellows joint), extensible tubing, distal bendable ribbon segments, and rigid segments coupled by flexible or elastic interconnects. As discussed previously, the two reciprocating rods 6 and 7 positioned inside of the internal tube 2 are also bendable either in their entireties or within their neck regions that are positioned within the bendable neck 11 of the internal tube 2. According to one preferred embodiment, as a bellow joint 11 bends, the inner rods 6 and 7 are forced to bend yet can still continue their reciprocating motion during operation. Thus the rods 6 and 7 can be designed such that they can reciprocate in a straight or curved configuration. Alternatively, (not shown) the bendable neck 11 comprises two or more segments that are interconnected by a pivot joint. In yet another embodiment (not shown) the internal tube can be bendable, incorporating the bendable reciprocating extension members (rods). In this embodiment, the bendable joints are not necessary and the internal tube with rods would bow to the desired angle. Alternatively, the rigid internal tube can have a flexible extension on its inferior end extending distally and inferior to the reciprocating rods. An arc or loop is fixed to the most distal end of the flexible extension and extends superiorly. A pull ribbon can be fixed to the top (superior end) of the arc or loop. The reciprocating ribbons continue from inside the inner tube over an extension ribbon over the flexible extension segment of the internal tube through the inside of the arc, where they then are fixed to the crossbars attached to the blades. Pulling the pull ribbon as described above bends the extension segment and the reciprocating ribbons that are stacked above it.

Any suitable apparatus can be used for articulating the bendable neck 11. As a non-exclusive example, a bendable pull ribbon 12 or cable can be fixed to the superior, distal end of the internal tube 2. The pull ribbon 12 is preferably coaxial with the internal tube 2 and traverses in a proximal/distal direction between the external tube 3 and the internal tube 2. Preferably, the pull ribbon 12 is not fixed to the proximal area of the internal tube 2 and has a floating catch 13 positioned at its most proximal end, preferably extending upwards. As shown in FIG. 2, when the external tube 3 is pulled proximally partially, the blades 4 and 5 are first released from inside the external tube 3. With further squeezing of the handle 18, the proximal end of the external tube 3 is further pulled proximally and engages with the catch 13 on the pull ribbon 12 thereby pulling the pull ribbon 12 further proximal. As shown in FIG. 3, this results in pulling of the distal end of the internal tube 2 and bending the neck 11 in a superior direction. The further the pull ribbon 12 gets pulled proximally, the more acute the α° angle of the neck 11. FIG. 3, shows the device 1 in a fully compressed configuration, wherein the tube spring 19 is fully compressed, the handle 18 (and handle spring 20) is maximally squeezed, the external tube 3 is in its furthest proximal position, and the neck 11 of the internal tube 2 is articulated at its limit. Both the tube spring 19 and/or the handle spring 20 can be used according with the embodiments herein. The rods 6 and 7 and coupled blades 4 and 5 are configured to rapidly reciprocate in any position (straight or curved) shown in FIGS. 1-3, or positions in between. In an alternative design not shown, each of the rods, near the distal end, has a segment that is bent to about 25 degrees in it neutral position. The outer tube straightens the rod when pushed distally over the bent segment. When the outer tube is pulled proximally exposing this segment, the rods bend toward their neutral position. In this design, the pull ribbon is used to stabilize the bend as counter traction during operation.

Figure 19:
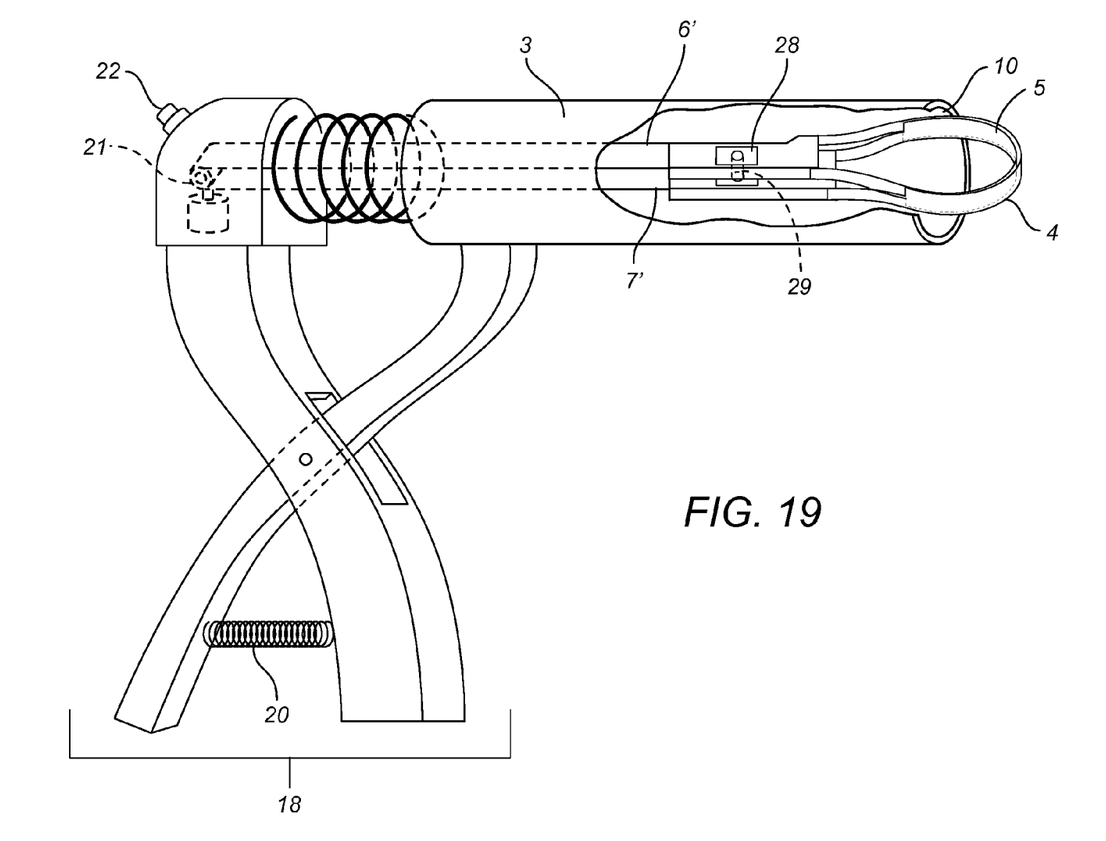
FIG. 19 is a perspective view of a cutting device, lacking an internal tube, in its natural position.

Alternatively, certain devices herein are not configured to bend upwards, such as shown in FIG. 19. According to these simplified embodiments, an internal tube is not needed, nor are pull ribbons, catches, or bendable necks. The extension members 6' and 7' can be ribbons or rods, and can be rigid, without the ability to bend significantly.

Figure 11:
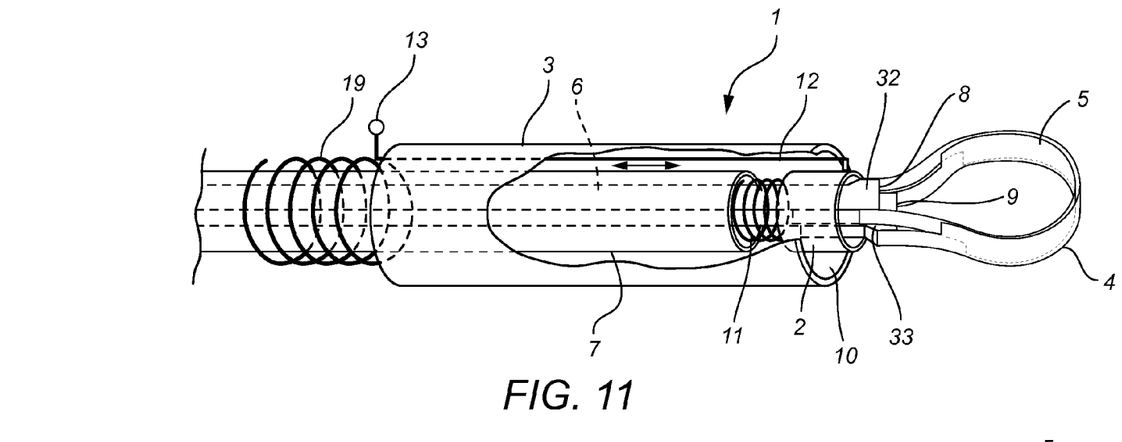
FIG. 11 is a close up view of a cutting device in a partially extended position.

When the handle 18 is released from a squeezed/compressed position shown in FIG. 3, the tube spring 19 pushes the external tube 3 distally. If the release is partial, the neck 11 straightens as the device 1 returns to the configuration shown in FIGS. 2 and 11. If the release is complete, the tube spring 19 pushes the external tube 3 to its maximal distal position, as shown in FIG. 1. During this release, it is preferred that the external tube 3 slides forward collapsing the flexible blades 4 and 5 so that they can fit inside the distal opening 10 of the external tube 3. Oval shaped blades 4 and 5 are preferred for this embodiment, as they do not require collapsible cross bars as do the U-shaped blades 4' and 5'. Otherwise for the U-shaped blades attached to the non-collapsible cross bars, the external tube 3 along with the enclosed collapsed blades 4 and 6 can be inserted or removed through a trocar sleeve having a larger diameter (not shown), of larger diameter than the length of the cross bars.

Figure 17:
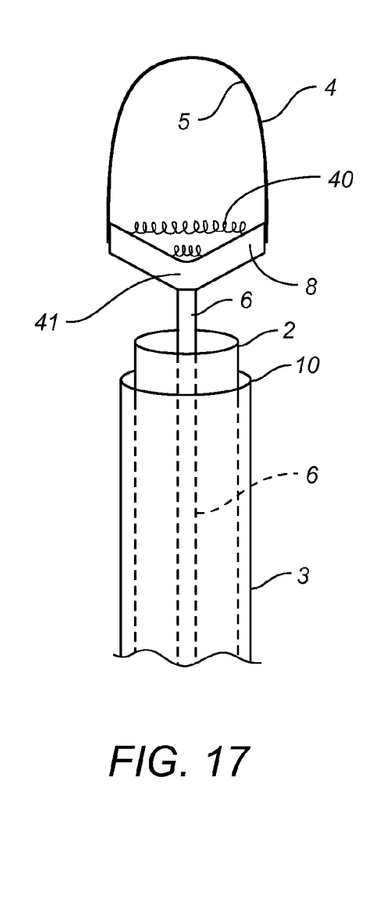
FIG. 17 is a top view of an external tube with a bendable crossbar in an open position.
Figure 18:
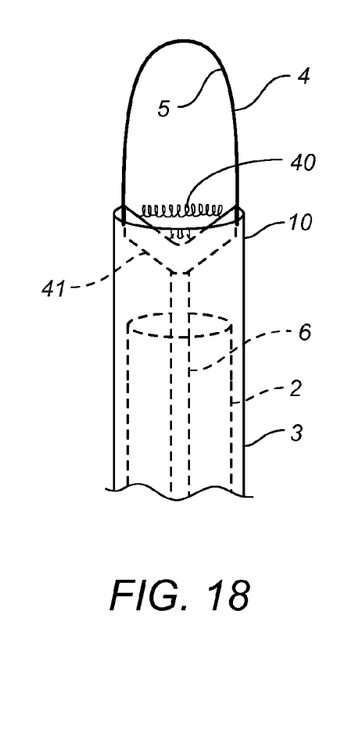
FIG. 18 a top view of an external tube with a bendable crossbar in a collapsing position.

Alternatively, the device can be configured to such that the external tube 3 can collapse the crossbars 8 and 9 and the attached U-shaped blades 4' and 5'. One non-exclusive method of collapsing the crossbars 8 and 9 is to have them made of a bendable material (e.g., fiberglass, thin metal, such as stainless steel, spring steel, or nitinol). According to this embodiment, and as shown in FIGS. 17 and 18, the crossbars 8 and 9 are forced to bend distally at its point of fixation 41 with the reciprocating extension members 6 and 7 as the outer tube 3 is pushed distally. A spring 40 can be positioned between the ends of the crossbar 8 to help maintain its open shape when exposed outside of the external tube 3.

Figure 15:
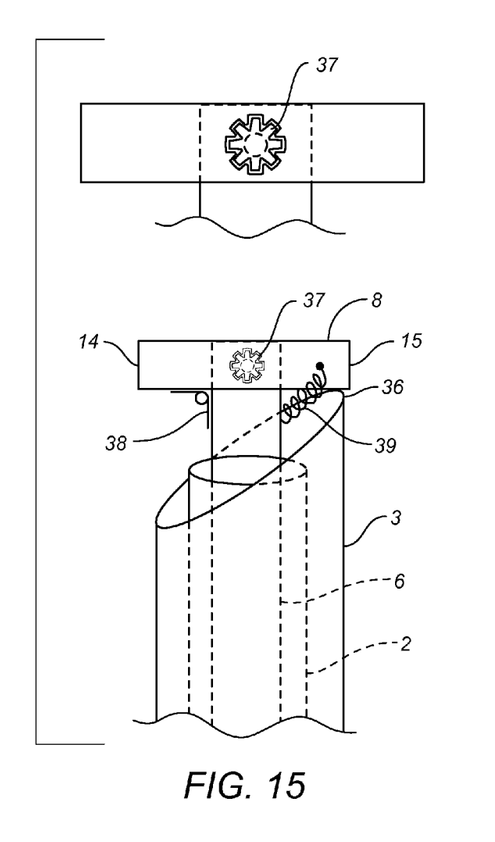
FIG. 15 is a top view of a beveled external tube with a swiveling crossbar in an open position.
Figure 16:
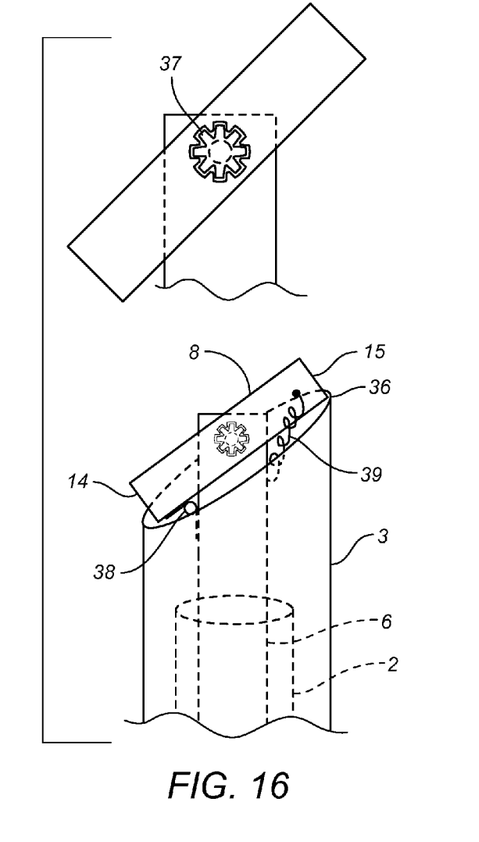
FIG. 16 a top view of a beveled external tube with a swiveling crossbar in a collapsing position.

Another way to collapse the U shaped blades 4' and 5' is to have the crossbars 8 and 9 swivel in one direction as the external tube is pushed distally, coming in contact with the crossbars. To accomplish this function, and as shown in FIGS. 15 and 16, the distal end of the external tube 3 can be beveled, such that the distal end of the bevel 36 comes in contact with one side of the crossbars 8 and 9 to collapse it. For example, if the crossbar is configured to swivel clockwise then the bevel is on the distal left of the external tube and if the crossbar 8 swivels counterclockwise (shown in FIGS. 15 and 16) then the bevel 36 in on the distal right of the external tube. As the external tube 3 moves distally, the bevel end 36 hits the right side 15 of the superior crossbar 8, thus pushing the left end 14 of the crossbar 8 proximally. Suitable springs can be used to allow for the crossbar 8 to collapse within the external tube 3 and expand perpendicularly to the extension members 6 and 7 after being released from the external tube 3 and remain rigid for operation. For example, a torsion spring 38 is positioned between the left end 14 of the crossbar 8 and the superior extension member 6 and a tension spring 39 is positioned between the right end 15 of the crossbar 8 and the superior extension member 6. While only one superior crossbar 8 is shown in FIGS. 15 and 16, the inferior crossbar can operate in the same way.

During cutting, the swiveling crossbars 8 and 9, should be locked in a fixed position perpendicular to the rods 6 and 7, so that the crossbars 8 and 9 can move with the rods. One way to lock the crossbars in a fixed position, is for a central ratcheted pin 37 that attaches the crossbars 8 and 9 to the distal end of the extension members 6 and 7 that has a keeps the cross bars stationary during operation and/or can have a locking mechanism on it.

According to preferred embodiments and as shown in FIG. 15, a catching bag 27 can be positioned below the blades 4 and 5. Preferably the bag 27 is coupled to the outside blade 4 using any suitable means such as glue, solder, or rivets. This embodiment may be advantageous in helping to prevent cut up pieces of tissue from contaminating surrounding areas. The bag 27 catches severed tissue after it is cut away by the blades 4 and 5. It is preferred that the bag 27 is elastic as it will distort with the reciprocating motion of the blades 4 and 5. Preferably the bag 27 is made of a solid, elastic material throughout, without holes, such as rubber, nylon, and the like.

The cutting devices 1 described herein, having dual reciprocating looped blades 4 and 5 that simultaneously move in opposite directions is highly advantageous over the prior art. The embodiments herein allow for increased travel back and forth compared to single looped blades, as the two blades 4 and 5 are now simultaneously cutting in opposing rotational directions. The dual blades 4 and 5 also helps prevent the targeted tissue from moving in the same direction as the cutting path of an oscillating single looped blade. Reciprocating looped blades 4 and 5 simultaneously moving in opposing rotational directions helps stabilize the designated area so that the cutting edges of the blades 4 and 5 can make purchase with the tissue. Experiments done with double looped blades moving in the same direction was found to be disadvantageous in that the blades tended to bend at the neck of the loop. Configuring the devices herein such that the double blades move simultaneously in opposite directions (clockwise and counter-clockwise) helps to prevent this undesired bending of the blades as the rods reciprocate in opposite directions. This beneficial stabilizing effect results from a more fluid motion of the blades moving back and forth in opposing directions along their contour.

Any suitable materials can be used to make the assemblies 1 described herein including plastics and metals. The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. A tissue cutting device comprising:
an electric motor configured to be turned on and off;
an external tube having an internal channel traversing lengthwise from proximal to distal ends;
first and second extension members having proximal and distal ends, left and right lateral sides, and positioned superiorly and inferiorly to one another within the internal channel of the external tube such that they traverse parallel with the length of the external tube, wherein the proximal ends of the extension members are operably coupled to the electric motor that drives straight reciprocating motion of the first and second extension members in alternate proximal and distal directions with respect to each other, such that when the first extension member is pushed distally the second extension member is pulled proximally, and vice versa;
an inner looped blade, having a first end and a second end, and a defined width at a most distal point, measured in the superior to inferior direction, and has a first extension of a predetermined length, extending from a superior side of the first end, and has a second extension extending from an inferior side of the second end, wherein the first and second extensions have widths that are less than the width of the looped inner blade at its most distal point, and are substantially the same as the thickness of the distal ends of the extension members measured in the superior to inferior direction, and wherein the extensions of the inner looped blade are coupled to a left or right lateral side of the extension members' distal ends;
an outer looped blade, equal to or longer in length than the inner looped blade, positioned distally and adjacent to the inner looped blade, with a first end and a second end, wherein the outer looped blade has a defined width at a most distal point, measured in a superior to inferior direction, and has a first extension of a predetermined length extending from an inferior side of the first end and has a second extension extending from a superior side of the second end, wherein the extensions have widths that are less than the width of the looped blade at its most distal point, and are substantially the same as the thickness of the distal end of the extension members measured in the superior to inferior direction, and wherein the extensions of the outer looped blade are coupled to the left or right lateral sides of the extension members' distal ends;
and wherein the outer and inner looped blades are positioned distally to the distal end of the external tube, and are parallel to each other, with sharp superior and/or inferior edges that are, in the same horizontal plane relative to each other, and are configured to reciprocate in alternate clockwise and counter-clockwise directions and in opposite directions relative to each other as the first and second extension members reciprocate proximally and distally.

2. The tissue cutting device of claim 1, wherein for a given length, the distal ends of the extension members are offset from each other and, from one lateral side to the other, remain of the same width of each other, wherein one lateral side of the distal end of the superior extension member extends out further laterally than its opposite side and for the same given length the opposite lateral side of the distal end of the inferior extension member extends out laterally an equidistant length as the lateral extension of the superior extension member, and extends out further laterally than its opposite side; and wherein the first extension of the outer looped blade is coupled to the further extended lateral side of the distal end of the superior extension member and the second extension of the outer looped blade is coupled to the further extended lateral side of the inferior extension member; and wherein the first and second extensions of the inner looped blade are individually coupled to less extended lateral sides of the superior and inferior extension members respectively.

3. The tissue cutting device of claim 2, wherein, for a given length the distal ends of the extension members are offset, by a first flange extending laterally in the distal end of the superior extension member and a second flange with the same measurements as the first flange extending laterally, in the opposite direction, in the distal end of the inferior extension member;

wherein the first extension of the outer looped blade is coupled to the first flange of the superior extension member and the second extension of the outer looped blade is coupled to the second flange of the inferior extension member; and wherein the first and second extensions of the inner looped blade are individually coupled to non-flanged sides of the distal ends of the superior and inferior extension members respectively.

4. The tissue cutting device of claim 2 wherein, one lateral side of the distal end of the superior extension member comprises a first cutout, of a predetermined length and width, and the opposite lateral side of the distal end of the inferior extension member comprises a second cutout with the same measurements as the first cutout; and wherein the inner looped blade extensions are coupled to the first and second cutouts and the outer looped blade extensions area coupled to the non-cutout lateral sides of the distal end of the extension members.

5. The tissue cutting device of claim 2, wherein the outer looped blade is of a length equal to or longer than the inner blade, and for a given length between both first and second ends, up to its entire length, the outer looped blade has a defined width, measured in the superior to inferior direction, that is wider than the thickness, measured in the superior to inferior direction, of the distal ends of the extension members.

6. The tissue cutting device of claim 2, wherein the distal ends of the extension members are collapsible crossbars, of substantially similar lengths, and are perpendicular to the extension members in the horizontal plane, and extend out laterally, further than the external tube; and wherein the first extension of the outer looped blade is coupled to a first lateral side of the superior crossbar and the second extension of the outer looped blade is coupled to an opposite, second lateral side of the inferior crossbar and wherein the first extension of the inner looped blade is coupled to a first lateral side of the inferior crossbar and the second extension of the inner looped blade is coupled to an opposite, second lateral side of the superior crossbar.

7. The tissue cutting device of claim 6, wherein a distal end of the external tube is beveled, extending, further, distally on one lateral side, and having a spring positioned between the collapsible superior and inferior crossbars and their respective extension members, wherein the crossbars are configure to swivel into an open position, substantially perpendicular to their respective extension members, outside of the external tube and swivel toward a more parallel position when the beveled end of the external tube is pushed distally and collides with one side of the crossbars pushing the same side distally, thereby collapsing the blades to fit within the external tube.

8. The tissue cutting device of claim 7 wherein the collapsible superior and inferior crossbars are each coupled to their respective extension members by a ratcheted pin that releasably locks each crossbar in the open substantially perpendicular position.

9. The tissue cutting device of claim 6, wherein the collapsible superior and inferior crossbars are angled in a V-shape opening distally and having proximal convergent points coupled to their respective extension members, and a compression spring positioned between the V-shape superior crossbar and a second spring positioned between the V-shape of the inferior crossbar, such that in the open position, with the external tube positioned proximally, the crossbars are at their widest angle and the blades are expanded open; and when the external tube is slid distally, it collides with the both sides of the crossbars, thereby reducing the angle, and collapsing the outer and inner looped blades to fit within the external tube.

10. The tissue cutting device of claim 2 wherein the external tube is configured to slide linearly towards a proximal and distal end, such that when the external tube is slid to its most proximal end the outer and inner looped blades are exposed distally from the distal end of the external tube, and when the external tube is slid toward the distal end, the looped blades are entirely or partially positioned within the internal chamber.

11. The tissue cutting device of claim 2, further comprising an internal tube having a proximal and distal end and traversing parallel within the length of the external tube, wherein the first and second extension members are positioned within the internal tube, and wherein the internal tube comprises a bendable segment that aligns with a bendable segment of each of the extension members near the distal end, but proximal to the blades, configured to articulate in the superior direction of a predetermined angle, and maintain reciprocating motion of the extension members and attached blades thereby articulating the distal ends of the extension members and blades in the same superior direction.

12. The tissue cutting device of claim 11, wherein the internal tube, blades, and extension members are made of a bendable material, such that the extension members and internal tube can be bent to a predetermined angle superiorly and the looped blades can collapse within the external tube.

13. The tissue cutting device of claim 11 further comprising a flexible pull ribbon that traverses inside of and parallel to the external tube and outside of, but adjacent to, the superior side of the internal tube, and coupled at its distal end to a superior distal end of the internal tube and contains a catch on its proximal end that is proximal to the external tube; and wherein a squeezable handle is configured such that a partial squeeze slides the external tube a partial proximal distance, thereby exposing the outer and inner looped blades distally into an open position; and wherein, with further squeezing of the handle, the external tube slides more proximal, exposing the bendable segment of the internal tube and simultaneously collides with the catch of the pull ribbon proximally and with further squeezing the external tube pulls the pull cable proximally which results in bending of the internal tube's distal end superiorly, thereby controlling the angle of the distal cutting end by how much the handle is squeezed or released.

14. The tissue cutting device of claim 2, wherein the distal ends of the extension members are non-collapsible crossbars, of substantially similar lengths, and are perpendicular to the extension members in the horizontal plane, and extend out laterally, further than the external tube; and wherein the first extension of the outer looped blade is coupled to a first lateral side of the superior crossbar and the second extension of the outer looped blade is coupled to an opposite, second lateral side of the inferior crossbar and wherein the first extension of the inner looped blade is coupled to a first lateral side of the inferior crossbar and the second extension of the inner looped blade is coupled to an opposite, second lateral side of the superior crossbar.

15. The tissue cutting device of claim 1, wherein the length of the blade extensions is at least equivalent to the distance traveled by the blades in a clockwise to counter clockwise direction.

16. The tissue cutting device of claim 1, wherein one of the outer or inner looped blades has a pin at its most distal end and the other looped blade has a slot configured for the pin to slide in, to keep the blades together and in the same cutting plane during motion.

17. The tissue cutting device of claim 1, wherein the outer and inner looped blades have a thickness of less than or equal to 1 mm and are made of a material selected from the group consisting of: metal, metal alloy, and composite material.

18. The tissue cutting device of claim 1, wherein the outer looped blade has an outer surface facing distally from the device, and the device further comprises a bag having a top opening coupled to the outer surface and is sufficiently pliable to be positioned within the internal chamber of the external tube.

19. The tissue cutting device of claim 1, wherein the extension members are flat, flexible metal ribbons wherein one of the superior or inferior ribbons has a pin and the ribbon has a slot configured to keep the ribbons together and allow the pin to reciprocate within, as the ribbons move in opposite directions proximally and distally.

20. The tissue cutting device of claim 1, wherein the outer blade has an inferiorly extending backstop extension positioned near the middle of the outer blade and extending under the inner blade and the inner blade as an inferiorly extending backstop extension positioned near the middle of the inner blade and extending under the outer blade, such that the inner and outer blades glide over the backstops and remain on the same cutting plane.

21. A method of cutting tissue from a patient comprising:
providing the tissue cutting device of claim 1;
inserting the distal end of the external tube into the patient;
pulling the external tube proximally exposing the looped blades;
turning the electrical motor on to reciprocate the outer and inner looped blades in alternating clockwise and counter-clockwise directions;
cutting the tissue from the patient with the reciprocating outer and inner looped blades;
pushing the external tube distally over the looped blades; and
removing the external tube from the patient.

* * * * *